(12) United States Patent
Sugasawa

(10) Patent No.: US 9,297,736 B2
(45) Date of Patent: Mar. 29, 2016

(54) PARTICLE SIZE DISTRIBUTION MEASURING DEVICE

(75) Inventor: Hirosuke Sugasawa, Kyoto (JP)

(73) Assignee: HORIBA, LTD. (JP)

( * ) Notice: Subject to any disclaimer, the term of this patent is extended or adjusted under 35 U.S.C. 154(b) by 413 days.

(21) Appl. No.: 13/036,038

(22) Filed: Feb. 28, 2011

(65) Prior Publication Data

US 2011/0213581 A1      Sep. 1, 2011

(30) Foreign Application Priority Data

Feb. 26, 2010   (JP) ................................ 2010-042315

(51) Int. Cl.
  *G06F 19/00*        (2011.01)
  *G01N 15/02*        (2006.01)
(52) U.S. Cl.
  CPC .................................. *G01N 15/0211* (2013.01)
(58) Field of Classification Search
  CPC ........................................................ G06F 15/00
  USPC ........................................ 702/128, 182–185
  See application file for complete search history.

(56) References Cited

U.S. PATENT DOCUMENTS

| | | | | | |
|---|---|---|---|---|---|
| 5,428,443 | A | * | 6/1995 | Kitamura et al. ............. | 356/336 |
| 5,841,893 | A | * | 11/1998 | Ishikawa et al. ............. | 382/145 |
| 6,529,619 | B2 | * | 3/2003 | Ishikawa et al. ............. | 382/141 |
| 6,906,799 | B2 | * | 6/2005 | Bonin et al. .................. | 356/336 |
| 8,006,195 | B1 | * | 8/2011 | Woodings et al. ............ | 715/777 |
| 2001/0048366 | A1 | * | 12/2001 | Ikeda et al. ................... | 340/627 |
| 2002/0003624 | A1 | * | 1/2002 | Yamaguchi ................... | 356/336 |
| 2002/0101590 | A1 | * | 8/2002 | Shimaoka ..................... | 356/336 |
| 2003/0090656 | A1 | * | 5/2003 | Ikeda et al. ................... | 356/336 |
| 2003/0167156 | A1 | * | 9/2003 | Alba .............................. | 703/2 |
| 2005/0046840 | A1 | * | 3/2005 | Kusuzawa ..................... | 356/334 |
| 2006/0028470 | A1 | * | 2/2006 | Bennett et al. ................ | 345/440 |
| 2006/0055697 | A1 | | 3/2006 | Yoshioka et al. | |
| 2007/0121108 | A1 | * | 5/2007 | Ishimaru et al. ............ | 356/237.2 |
| 2007/0165225 | A1 | * | 7/2007 | Trainer ......................... | 356/335 |

(Continued)

FOREIGN PATENT DOCUMENTS

| | | |
|---|---|---|
| CN | 2251721 Y | 4/1997 |
| EP | 0316173 A1 | 5/1989 |

(Continued)

OTHER PUBLICATIONS

The United Kingdom Search Report for United Kingdom application No. GB1102787.7 dated Apr. 27, 2011.

(Continued)

*Primary Examiner* — Edward Raymond
(74) *Attorney, Agent, or Firm* — Cantor Colburn LLP

(57) ABSTRACT

To facilitate evaluation of a measurement condition in order to set an optimum measurement condition for each sample. A particle size distribution measuring device is provided with: an device main body that measures a particle size distribution of a sample; and an interface device that receives an input from an operator to perform drive control of the device main body, and receives a measurement result from the device main body to display the measurement result, wherein the interface device displays, in a graph, a relationship between values of operational parameters, which are to be set to measure the particle size distribution, and values of evaluation parameters obtained by using the measurement result from the device main body, which correspond to each of the values of the operational parameters.

4 Claims, 8 Drawing Sheets

(56) References Cited

U.S. PATENT DOCUMENTS

| | | | |
|---|---|---|---|
| 2007/0179715 A1* | 8/2007 | Ariyoshi | 702/19 |
| 2011/0063715 A1* | 3/2011 | Tanaka et al. | 359/296 |
| 2011/0074948 A1* | 3/2011 | Izuka | 348/135 |
| 2011/0148881 A1* | 6/2011 | Kageyama | 345/440 |

FOREIGN PATENT DOCUMENTS

| | | |
|---|---|---|
| JP | 6-74892 A | 3/1994 |
| JP | 10-197438 A | 7/1998 |
| JP | 11183356 A | 7/1999 |
| JP | 2003-194702 A | 7/2003 |
| JP | 2003-232718 A | 8/2003 |
| JP | 2004-184134 A | 7/2004 |
| JP | 3633169 B2 | 1/2005 |
| JP | 2008-111810 A | 5/2008 |
| JP | 2008-164539 A | 7/2008 |
| JP | 2010-271159 A | 12/2010 |

OTHER PUBLICATIONS

Examination Report under Section 18(3) for United Kingdom patent application No. GB1102787.7, dated Jun. 14, 2013.
Office Action for Japanese Application No. 2010-042315, dated Nov. 5, 2013 (see English Summary).
Office Action for the Chinese Patent Application No. 201110035781.4 dated Dec. 26, 2013, with English abstract.
Guobiao, L., et al., "Particle Size Analysis by Laser Light Scattering", Materials Review, vol. 20, No. 4, Apr. 20, 2006, pp. 90-93.
Shu, X., "Mastersizer 2000 laser particle size analyzer and its applications", Journal of Hefei University of Technology, vol. 30 No. 2, Feb. 2007, pp. 164-167.
Japanese Office Action dated Dec. 15, 2015, issued in patent application No. 2010-042315.

* cited by examiner

PARTICLE SIZE DISTRIBUTION MEASURING DEVICE

TECHNICAL FIELD

The present invention relates to a particle size distribution measuring device.

BACKGROUND ART

This sort of particle size distribution measuring device has a large number of evaluation parameters (including particle sizes such as a mean diameter and a mode diameter, and the like) for determining whether or not setting items (such as a sample circulation rate and an ultrasonic application time) for setting a measurement condition to measure a particle size distribution, and a measurement result are reasonable. For this reason, it is extremely difficult to set an optimum measurement condition for a sample, and evaluate the measurement condition.

As a particle size distribution measuring device that facilitates input to the setting items for setting a measurement condition, as disclosed in Patent literature 1, there is one that is adapted to provide a guidance display for each of the setting items, and on the basis of the guidance display, set a most likely measurement condition through an operator to measure a particle size distribution.

However, even in the case of simplifying the input to the setting items for a measurement condition, it should be determined whether or not the setting condition is optimum for a sample, on the basis of a relationship with a measurement result including particle sizes such as a mean diameter and a mode diameter. For this reason, there still remains a problem that, in order to obtain an optimum measurement result, a measurement condition should be set by trial and error, and therefore setting the measurement condition is difficult.

CITATION LIST

Patent Literature

Patent literature 1: JP 2003-194702 A

SUMMARY OF INVENTION

Technical Problem

Therefore, the present invention is made to solve the above-described problem, and has a main object to, in order to set an optimum measurement condition for each sample, facilitate evaluation of the measurement condition.

Solution to Problem

That is, a particle size distribution measuring device is provided with: an device main body that measures a particle size distribution of a sample; and an interface device that receives an input from an operator to perform drive control of the device main body, and receives a measurement result from the device main body to display the measurement result, wherein the interface device displays, in a graph, a relationship between values of operational parameters, which are to be set to measure the particle size distribution, and values of evaluation parameters obtained by using the measurement result from the device main body, which correspond to each of the values of the operational parameters.

Note that the operational parameters are parameters of which an input operation should be performed by an operator, and includes: measurement condition parameters that determine a measurement condition for the device main body to measure the particle size distribution; and calculation condition parameters for calculating the measurement result. The measurement condition parameters include, for example, a sample circulation rate, an operating time of an ultrasonic oscillator (an application time of an ultrasonic wave), an intensity of the ultrasonic wave, the number of data extraction times, the presence or absence of operation of the ultrasonic oscillator during the measurement, a sample concentration, and the like, and the calculation condition parameters include, for example, a refractive index of the sample (particles, solvent), and the like. Also, the evaluation parameters are intended to determine whether or not the measurement condition is optimum for each sample, and include, for example, particle sizes such as a mean diameter, a median diameter, and a mode diameter, a standard deviation of the particle size distribution, a residual sum of squares of the particle size distribution, a distribution function (for example, a ratio of particles having a predetermined particle size), and the like.

If so, the relationship between the values of the operational parameters and the values of the evaluation parameters corresponding to each of the values of the operational parameters is displayed in the graph, and thereby on the basis of the values of the evaluation parameters displayed on the graph, it can be easily evaluated which operational parameter value is optimum. Accordingly, by displaying a relation ship with the evaluation parameters in a graph for each of the various operational parameters, and selecting an optimum value of each of the operational parameters on the basis of values of the evaluation parameters, an optimum measurement condition can be easily set for each sample.

Also, the interface device is preferably configured to be able to change types of the operational parameters and/or types of the evaluation parameters to be displayed in the graph. If so, by changing the types of the operational parameters, it becomes unnecessary to display a graph for each of the operational parameters, so that the number of graphs to be displayed on a screen can be reduced, and therefore visibility can be enhanced. Also, by changing the evaluation parameters, a relationship with an easy-to-evaluate evaluation parameter can be displayed for each of the operational parameters, which makes it easy to select an optimum value.

In order to evaluate the operational parameters while understanding a whole image of the measurement result, and thereby make it easy for an operator to make evaluations, the interface device preferably displays the measurement result from the device main body and the graph on the same screen.

Advantageous Effects of Invention

According to the present invention configured as described, in order to set an optimum measurement condition for each sample, evaluation of the measurement condition can be facilitated.

DESCRIPTION OF EMBODIMENTS

One embodiment of a particle size distribution measuring device according to the present invention will hereinafter be described with reference to the drawings.

A particle size distribution measuring device 100 according to the present embodiment is one that measures an angle distribution or fluctuation in intensity of diffracted or scattered light generated when a sample is irradiated with light, and calculates a result of the measurement on the basis of the Doppler principle or MIE scattering theory to thereby measure a particle size distribution of a particle group contained in the sample, and provided with: an device main body 2 that performs various processing steps associated with the actual measurement; and an interface device 3 that is communicably connected to the device main body 2 to control content and processing procedure of each of the processing steps in the device main body 2 and also receives a result of the measurement from the device main body 2 to display the result.

First, each part of the device main body 2 is described.

Figure 2:
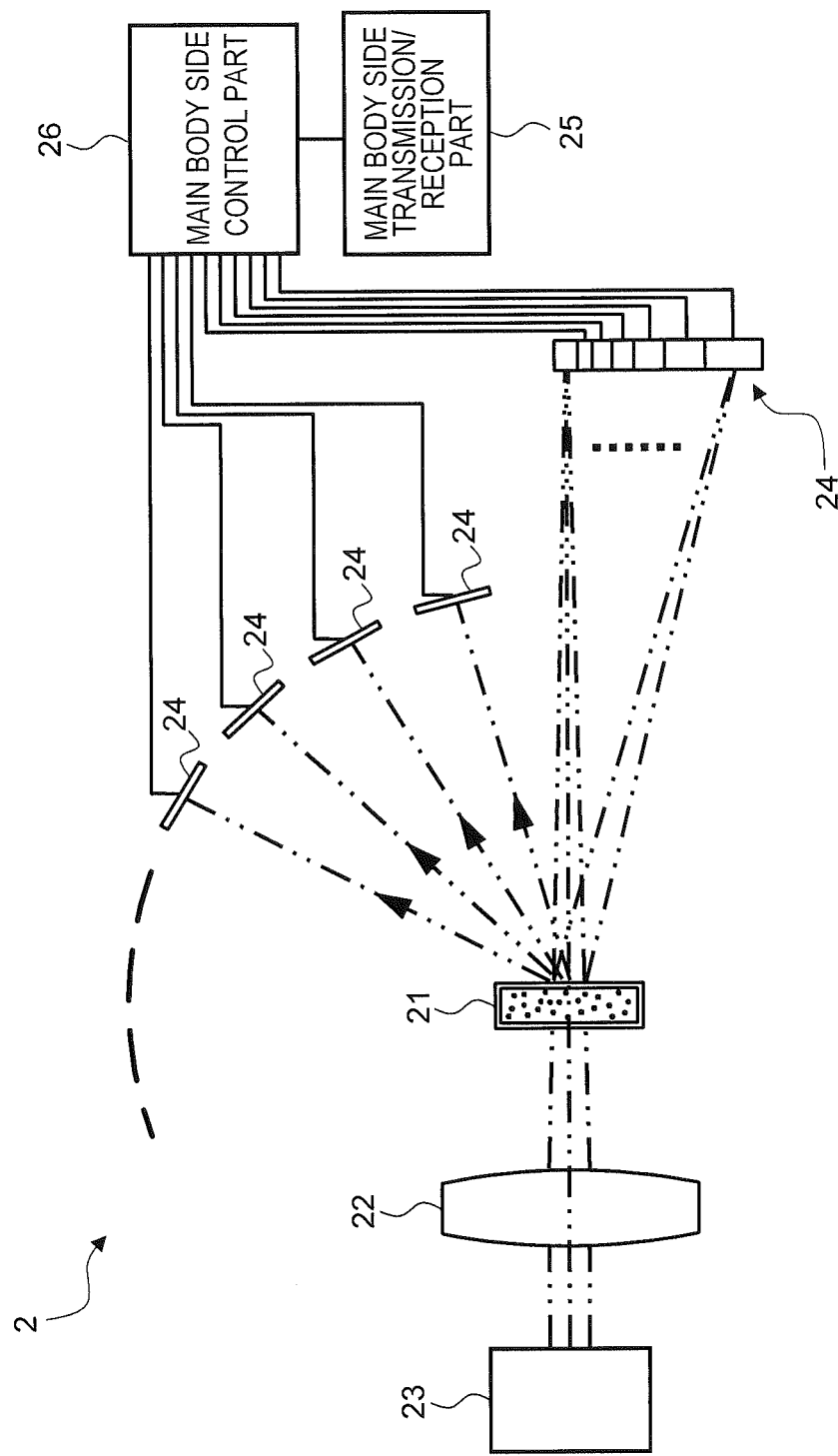
FIG. 2 is an device main body schematic diagram illustrating respective parts of an device main body in the same embodiment.

The device main body 2 is of a so-called diffraction/scattering type that is, as illustrated in FIG. 2, provided with: a cell 21 inside which the particle group serving as a measuring object is dispersed; a semiconductor laser 23 that serves as a light source and irradiates the particle group with the light through a lens 22; a plurality of detectors 24 that detect an intensity distribution among transmitted light having transmitted through the cell 21 and diffracted/scattered light diffracted or/and scattered by the cell 21; and a dedicated main body side computer that, at least on the basis of light intensity signals outputted from the respective detectors 24, calculates the particle distribution, monitors/controls each of the above-described devices inside the device main body 2, or transmits/receives various pieces of data to/from the interface device 3.

The cell 21 is a transparent one that contains the sample formed by dispersing the particle group serving as the measuring object in a dispersion medium such as water, and detachably attached at a predetermined position of a cell containing chamber (not illustrated) by an unillustrated cell holder or the like. In the present embodiment, the cell 21 is assumed to be of a circulating wet type, and provided in an unillustrated sample circulating flow path. In the sample circulating flow path, a stirring motor, a circulating pump, a particle group inlet, and the like (all of which are not illustrated) are provided to circulate the sample inside the cell 21.

The semiconductor laser 23 is one that emits coherent light and can adjust a light axis and an intensity of the irradiation light.

The plurality of detectors 24 are discretely arranged on the light axis of the semiconductor laser 23 and within a predetermined angle range from the light axis around the cell 21, for example, in the same circumference, and detect an intensity of the transmitted light that travels straight on the light axis and an angle-based intensity of the scattered light that is scattered in various angle directions by the sample. Each of the detectors 24 outputs a light intensity signal depending on an intensity of incident light.

The main body side computer is a dedicated computer that is structurally provided with a CPU, a memory, an A/D converter, an I/O interface, a communication interface, and the like, and fulfills a function as a main body side control part 26 or a main body side transmission/reception part 25 by the CPU and peripheral devices operating on the basis of a predetermined program stored in the memory.

The main body side control part 26 is provided with: an interpretation function that interprets a command transmitted from the interface device 3 to be described later; a monitoring/control function that, on the basis of a result of the interpretation, or the like, monitors/controls the detectors 24, semiconductor laser 23, stirring motor, circulating pump, and the like; a particle size distribution calculation function that receives the light intensity signals outputted from the respective detectors 24, and from values of the signals, according to an algorithm based on the MIE scattering theory, calculates pieces of particle size distribution data representing a particle size distribution; and other functions.

The main body side transmission/reception part 25 is configured with use of the communication interface, and receives the pieces of particle distribution data from the main body side control part 26 to transmit them to the interface device 3, or receives a command from the interface device 3 to transmit it to the main body side control part 26 in order to adjust the light axis of the semiconductor laser 23, perform rotation control of the stirring motor, or perform other control.

Next, the interface device 3 is described.

Figure 3:
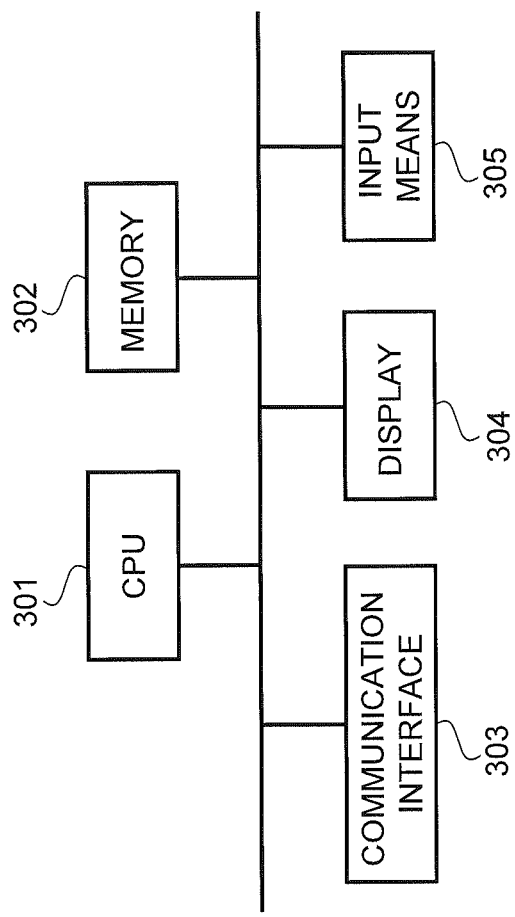
FIG. 3 is a hardware configuration diagram of an information processor in the same diagram.

The interface device 3 is a general-purpose computer such as a personal computer, and as illustrated in FIG. 3, structurally provided with a CPU 301, a memory 302, USB ports for making connections to a communication network and the main body side computer, a communication interface 303 such as a modem, a display 304, input means 305 such as a mouse and a keyboard, and the like.

Figure 1:
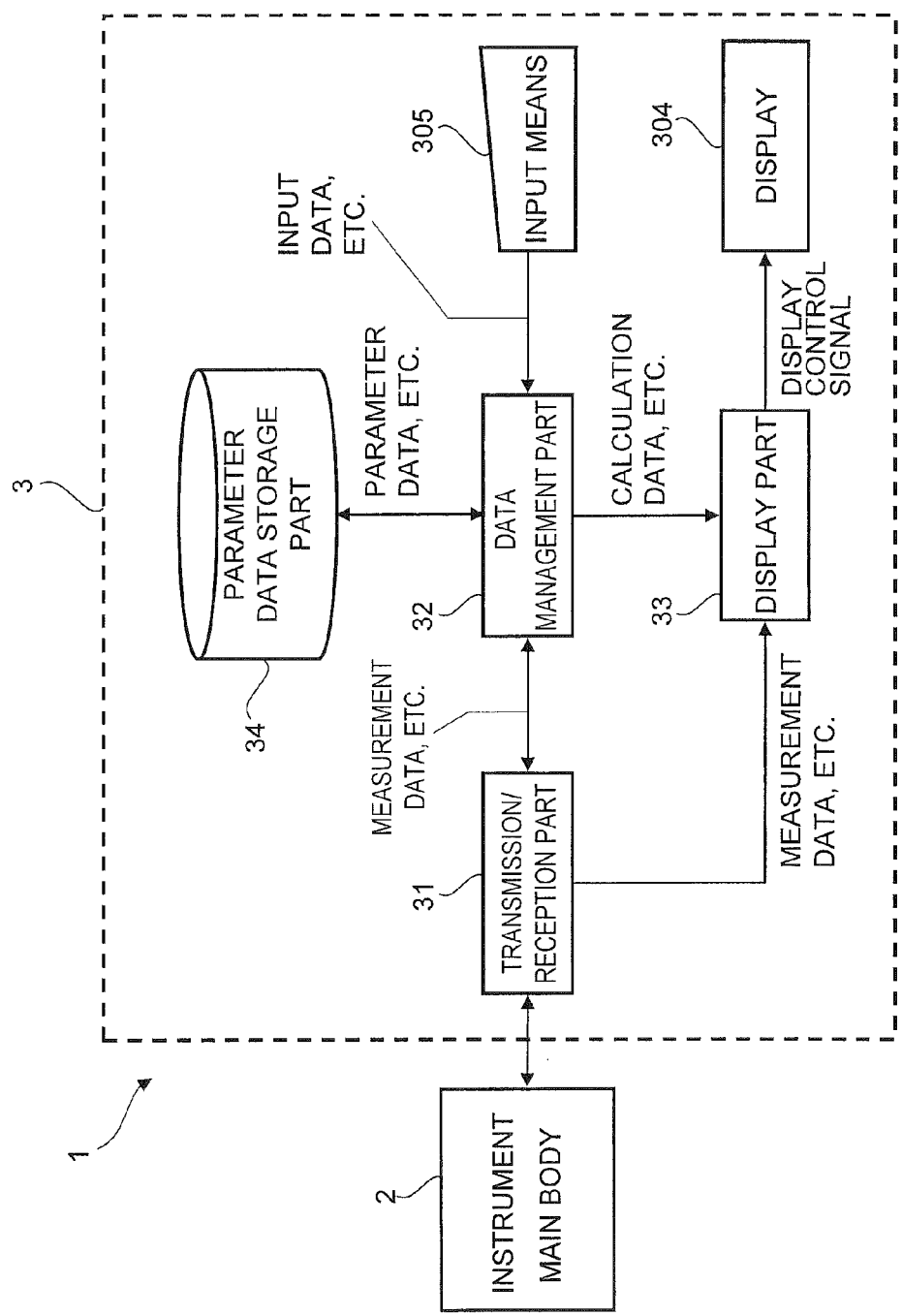
FIG. 1 is a schematic diagram illustrating the whole of a particle size distribution measuring device and functional blocks of an interface device in one embodiment of the present invention.

Also, a predetermined program is installed in the memory 302, and on the basis of the program, the CPU 301 and the peripheral devices collaboratively operate, whereby as illustrated in FIG. 1, the interface device 3 functions as a transmission/reception part 31, a data management part 32, a display part 33, a parameter data storage part 34, and other parts.

The respective parts 31 to 34 are described.

The transmission/reception part 31 is one configured with use of the communication interface 303, which for each of the processing steps performed by the device main body 2, transmits one or more commands constituting the step (processing elements constituting the step (such as setting of a rotation number of the stirring motor, and setting of a flow rate by controlling the circulating pump)) to the device main body 2 along with corresponding parameters, and also receives result data representing a result of the processing step performed on the basis of the transmitted commands by the device main body 2.

The data management part 32 acquires, from the transmission/reception part 31, measurement result data that is obtained under an initial measurement condition (initial parameter values) preliminarily set by an operator, and with use of the measurement result data, varies a value of each of the operational parameters to calculate the measurement result data at the value. Then, the data management part 32 outputs the calculated data (representing a value of each of the operational parameters, and a value of an evaluation parameter corresponding to the operational parameter value) to the display part 33.

Also, the data management part 32 receives input values (operator selection values) of the operational parameters inputted by the operator who operates the input means 305, and outputs them to the parameter data storage part 34 to store them in the parameter data storage part 34. Alternatively, in the case where predetermined values have already been stored, the values are updated to the operator selection values, which are then stored.

In addition, the data management part 32 is also one that manages various types of data, such as acquiring, from a sequence data storage part (not illustrated), sequence data that is selected by the operator or predetermined, acquiring a value of a parameter that is set on an input screen (not illustrated) and attaching it to a command, and newly storing or storing in an update state, in the sequence data storage part, sequence data that is newly set on the input screen. Note that the sequence data refers to data indicating a procedure of a processing step performed by the device main body 2.

The parameter data storage part 34 is one that is set in a predetermined region of the memory 302 and stores pieces of data indicating parameter values of the operational parameters inputted by the operator who operates the input means 305. Specifically, the parameter data storage part 34 stores parameter values of the operational parameters indicating a measurement condition corresponding to each sample with relating the parameter values to the sample. For example, the parameter data storage part 34 stores, as an operational condition for a sample X, a group of parameter values including a parameter value a (X) of an operational parameter a, a parameter value b (X) of the operational parameter b, a parameter value c (X) of an operational parameter c, and the like.

The operational parameters are parameters of which an input operation should be performed by the operator, and include measurement condition parameters that determine a measurement condition for the device main body to measure the particle size distribution, and calculation condition parameters for calculating a measurement result. The measurement condition parameters include, for example, a sample circulating rate (circulating pump speed), an operating time of an ultrasonic oscillator (an application time of an ultrasonic wave), an intensity of the ultrasonic wave, the presence or absence of operation of the ultrasonic oscillator during the measurement, the number of data extraction times, a sample concentration, and the like. Note that a parameter value in the presence or absence of operation of the ultrasonic oscillator during the measurement corresponds to "the presence of operation" or "the absence of operation".

On the other hand, the evaluation parameters are ones that are intended to determine whether or not a measurement condition is optimum for each sample, and include particle sizes such as a mean diameter, a median diameter, and a mode diameter, a standard deviation of a particle size distribution, a residual sum of squares of the particle size distribution, a distribution function (for example, a ratio of particles having a predetermined particle size), and the like.

The display part 33 is one that controls the display 304, and has an input screen display function (function as an input screen display part), a result display function (function as a result display part), and other functions. The input screen display function is a function that displays the input screen for inputting the parameters necessary to set a measurement condition. The result display function is a function that displays, in a predetermined format, content of pieces of measurement result data such as pieces of particle size distribution data transmitted from the device main body 2.

Here, the result display function is described.

The display part 33 displays, on a screen of the display 304, a particle size distribution graph obtained from the pieces of measurement result data acquired from the transmission/reception part 31, and also displays, on the screen of the display 304, an evaluation graph obtained from the pieces of measurement result data.

Figure 4:
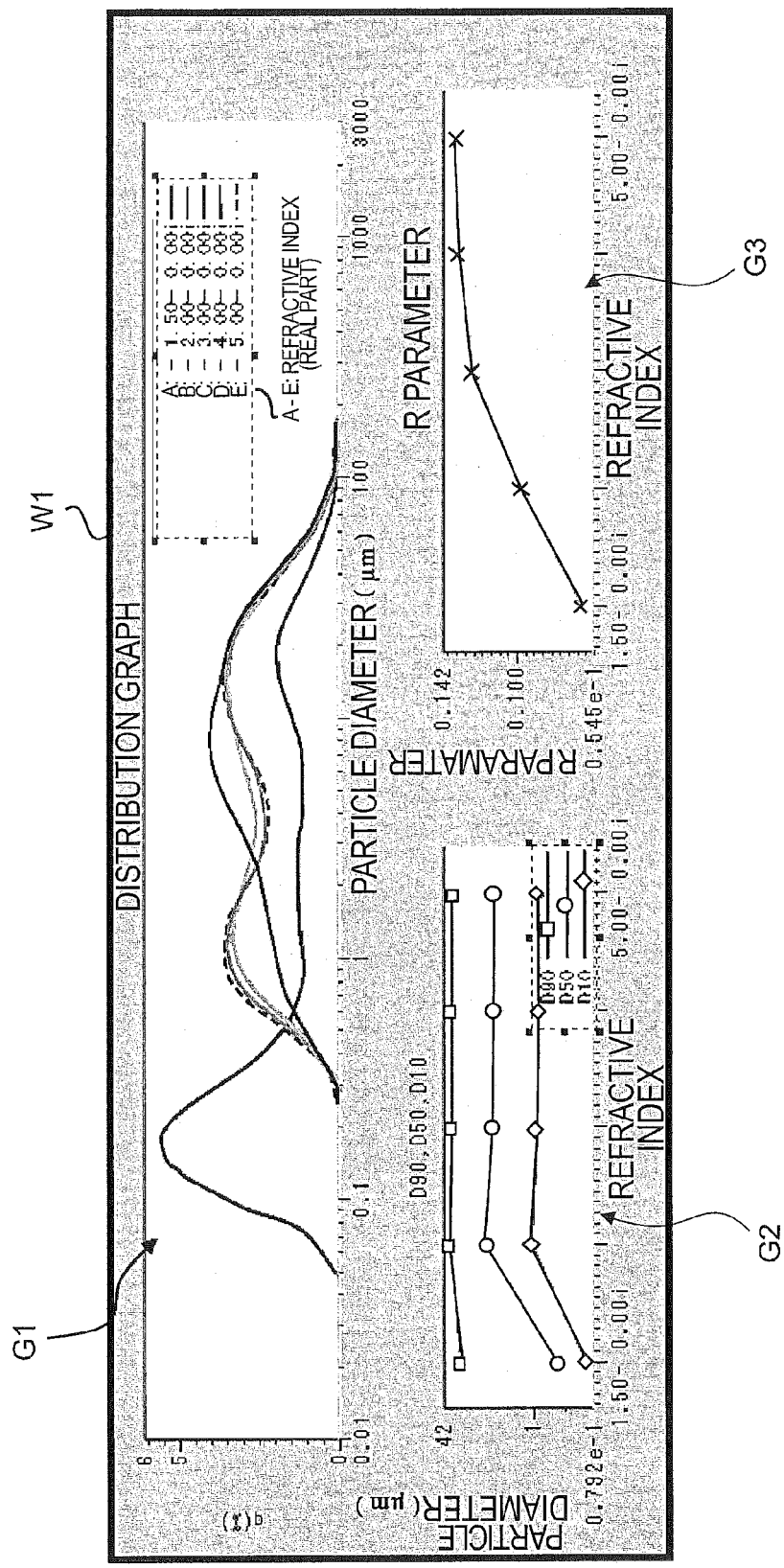
FIG. 4 is a diagram illustrating a graph summary display screen in the same embodiment.
Figure 5:
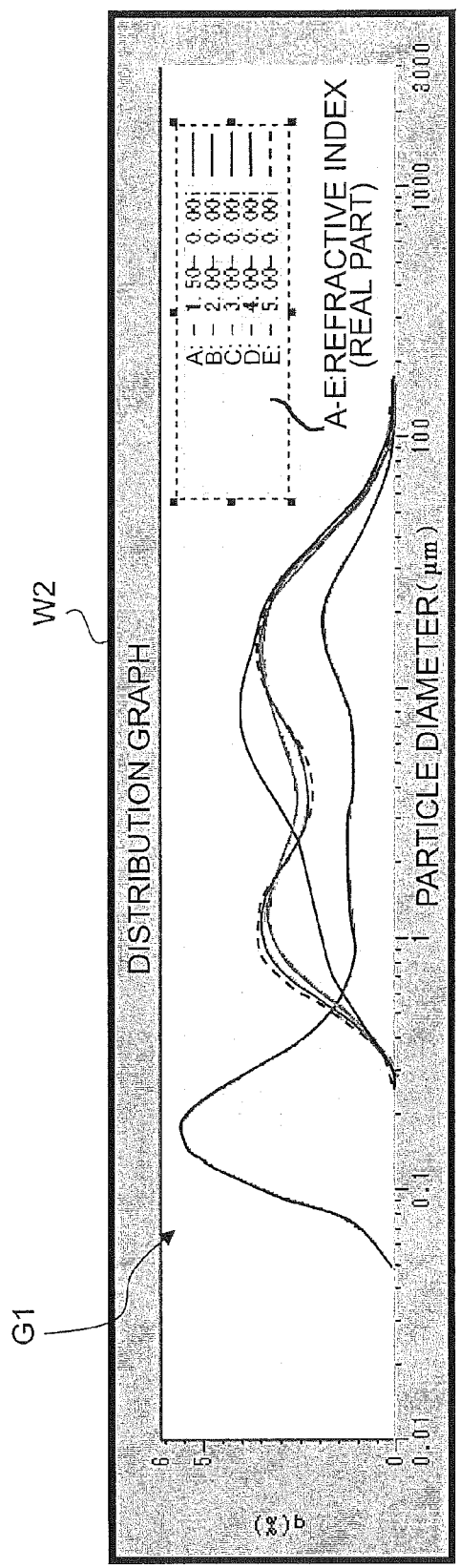
FIG. 5 is a diagram illustrating a measurement result graph display screen (particle size distribution graph) in the same embodiment.
Figure 6:
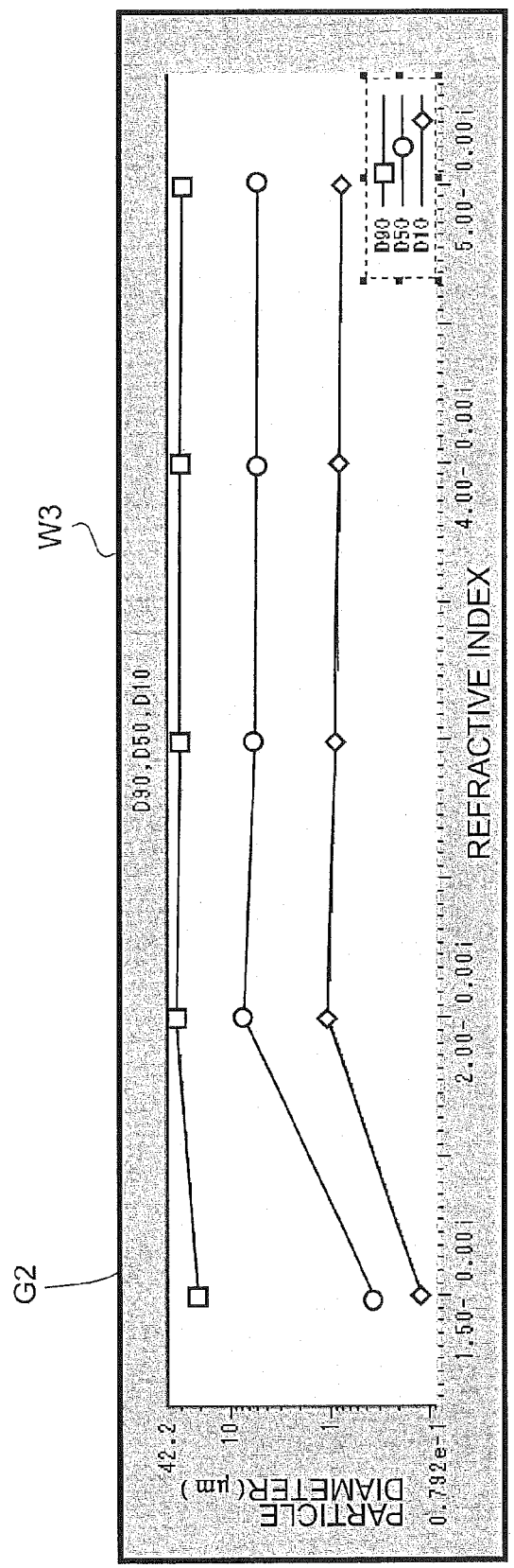
FIG. 6 is a diagram illustrating an evaluation graph display screen (percent particle diameter graph) in the same embodiment.
Figure 7:
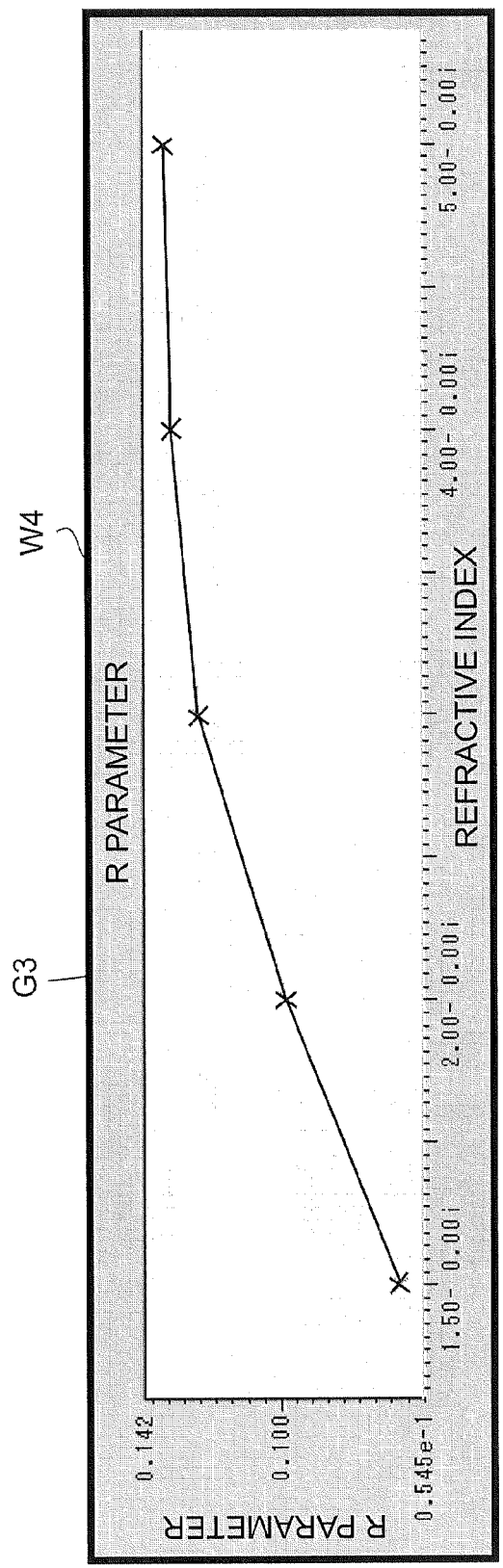
FIG. 7 is a diagram illustrating an evaluation graph display screen (residual parameter graph) in the same embodiment.

Specifically, the display part 33 displays, as illustrated in FIG. 4, a graph summary display screen W1 that displays a list of a measurement result graph G1 such as the particle size distribution graph and one or more evaluation graphs G2 and G3; as illustrated in FIG. 5, a measurement result graph display screen W2 that individually displays the measurement result graph G1; and as illustrated in FIG. 6 or 7, an evaluation graph display screen W3 or W4 that individually displays the evaluation graph G2 or G3, on the display 304 so as to be switchable.

The evaluation graph G2 or G3 of the present embodiment is a two-dimensional graph, and configured such that, under the condition that one of axes (e.g., horizontal axis) represents a predetermined operational parameter, and the other axis (e.g., vertical axis) represents a predetermined evaluation parameter, at each value of the operational parameter, a calculation value of the evaluation parameter (e.g., particle diameter) corresponding to the value is displayed on the graph.

The graph summary display screen W1 is configured to display on the same screen the list of the one measurement result graph (particle size distribution graph) G1, and the two evaluation graphs G2 and G3. The evaluation graph G2 displayed in the lower left of the graph summary display is a two-dimensional graph illustrating a particle size distribution characteristic, and illustrates the case where, under the condition that a horizontal axis represents a refractive index and a vertical axis represents a particle diameter, percent particle diameters (particle sizes D10, D50, D90) are displayed. That is, this is a result of, in the particle size distribution graph indicating a relationship between a particle diameter and a passing portion integration level (%), calculating a particle size at a passing portion integration level of 10% (particle size D10 (typical small particle diameter)), a particle size at a passing portion integration level of 50% (particle size D50 (typical median particle diameter)), and a particle diameter at a passing portion integration level of 90% (particle size D90 (typical large particle diameter)) according to corresponding specified refractive indices. By comparing a value of the particle diameter among D10, D50, and D90, it can be evaluated which refractive index is appropriate. Values of the passing portion integration level (%) are preferably 10%, 50%, and 90%, but not limited to them. Instead, a typical particle diameter (particle diameter at each of predetermined points on a graph in which pieces of particle size distribution data are displayed in an integrated distribution graph format) may be changed, and also the number of typical particle diameters is not limited to three, but may be decreased or increased.

On the other hand, the evaluation graph G3 displayed in the lower right is a two-dimensional graph illustrating a calculation result characteristic, and illustrates the case where for horizontal and vertical axes, a refractive index and a residual sum of squares (R parameter) are respectively displayed. The residual sum of squares indicates a variation in particle size distribution value from a value of Y' obtained by a regression equation under the condition that an X-axis represents a light intensity distribution and a Y-axis represents a particle size distribution, and also indicates that as a value of the variation decreases, the regression equation is more adapted. The reason why, in the present embodiment, the two evaluation graphs G2 and G3 are displayed as described is to display graphs having different characteristics to be evaluated.

Also, the operator operates a cursor (mouse pointer or the like) to press an unillustrated display switch button, and thereby the display part 33 switches from the graph summary display screen W1 to individually display only each of the graphs G1 to G3 displayed on the graph summary display screen W1. Specifically, the display part 33 switches from the graph summary display screen W1 (see FIG. 4) to the measurement result graph display screen W2 (see FIG. 5) or evaluation graph display screen W3 or W4 (see FIG. 6 or 7) to provide an enlarged display of the measurement result graph G1 or evaluation graph G2 or G3.

Further, the display part 33 is configured to, in the evaluation graph G2, change the types of the operational and evaluation parameters to display the parameters. Specifically, the operator operates the cursor (mouse pointer or the like) to press an unillustrated operational parameter change button, and thereby the display part 33 sequentially changes the operational parameters. Similarly, the operator operates the cursor (mouse pointer or the like) to press an unillustrated evaluation parameter change button, and thereby the display part 33 sequentially changes the evaluation parameters. Note that the display change of the operational parameters or evaluation parameters may be configured such that, for example, by pressing the corresponding parameter change button, a pull-down list that enables any of a plurality of parameter names to be selectively inputted is displayed and a parameter name can be selected from the pull-down list.

Next, the evaluation of the measurement condition using the particle size distribution measuring device 100 of the present embodiment is described.

First, the operator performs a necessary initial operation such as selecting a sequence on an initial screen (not illustrated) displayed on the display 304 of the interface device 3. Then, the data management part 32 acquires, from the sequence data storage part 34, data on the sequence selected by the operator. Also, when the operator uses the input means to input initial values of respective operational parameters, which should be set in the above sequence, the data management part 32 attaches the initial values to the commands. Note that the initial values to be attached to the commands may be, besides the initial values inputted by the operator, parameter values that are preliminarily stored in the parameter data storage part 34 and have been used in the past.

Then, the transmission/reception part 31 transmits the commands attached with the parameters to the device main body 2.

In the device main body 2, the main body side transmission/reception part 25 receives the transmitted commands and the like, and the main body side control part 26 interprets the commands and the like to monitor/control the detectors 24, the semiconductor laser 23, the stirring motor, the circulating pump, and the like. Also, the main body side control part 26 receives light intensity signals outputted from the respective detectors 24, and from values of the signals, at least calculates pieces of particle size distribution data representing a particle size distribution according to the algorithm based on the MIE scattering theory. Then, pieces of measurement result data including the pieces of particle size distribution data are transmitted back to the interface device 3.

Upon receipt of the pieces of measurement result data, the transmission/reception part 31 outputs the pieces of measurement result data to the data management part 32 and the display part 33.

Then, the data management part 32 uses the pieces of measurement result data to change the values of the respective operational parameters within predetermined ranges, and calculates values of the evaluation parameters at respective values of the operational parameters. Subsequently, the data management part 32 outputs to the display part 33 pieces of calculation data that are configured with relating the respective values of the respective operational parameters to the calculation values of the respective evaluation parameters.

Then, upon receipt of the pieces of measurement result data and pieces of calculation data, the display part 33 displays the measurement result graph G1 and evaluation graphs G2 and G3 on the graph summary display screen W1. At this time, the measurement result graph G1 displayed on the graph summary display screen W1 is not limited to the particle size distribution graph, but may be another graph such as a light intensity distribution graph representing light intensities of the respective detectors 24, or such graphs may be configured to be switchably displayed. Also, types of the evaluation graphs G2 and G3 to be initially displayed can be appropriately selected.

Also, when the operator performs the screen display switching operation, the display part 33 switches between the graph summary display screen W1, the measurement result graph display screen W2, and the evaluation graph display screens W3 and W4 to display any of them.

The operator presses the evaluation parameter change button on the basis of the evaluation graphs G2 and G3 on the graph summary display, or individually displayed evaluation graph G2 or G3, and thereby while changing the types of the evaluation parameters, inputs optimum values of the operational parameters on the unillustrated input screen. The input values are stored in the parameter data storage part 34 by the data management part 32. Then, the operator presses the operational parameter change button, and thereby the display part 33 changes the types of the operational parameters corresponding to the horizontal axes of the evaluation graphs G2 and G3 to display the graphs.

As described, an optimum value is selected and inputted for each of the operational parameters while changing all of the operational parameters. Also, an optimum value of each of the operational parameters is selected for each sample by the above operation, and thereby an optimum measurement condition can be obtained for each sample. The measurement condition obtained in this manner is used in next or subsequent measurement of a corresponding sample as parameters to be attached to commands of a sequence.

Effects of the Present Embodiment

According to the particle size distribution measuring device 100 configured as described according to the present embodiment, a relationship between values of the operational parameters and values of the evaluation parameters corresponding to each of the values of the operational parameters is displayed on a graph, and thereby on the basis of the values of the evaluation parameters displayed on the graph, it can be easily evaluated which operational parameter value is optimum. Accordingly, by displaying a relationship with the evaluation parameters in a graph for each of the various operational parameters, and selecting an optimum value of each of the operational parameters on the basis of values of the evaluation parameters, an optimum measurement condition can be easily set for each sample.

<Other Variations>

Note that the present invention is not limited to the above-described embodiment.

Figure 8:
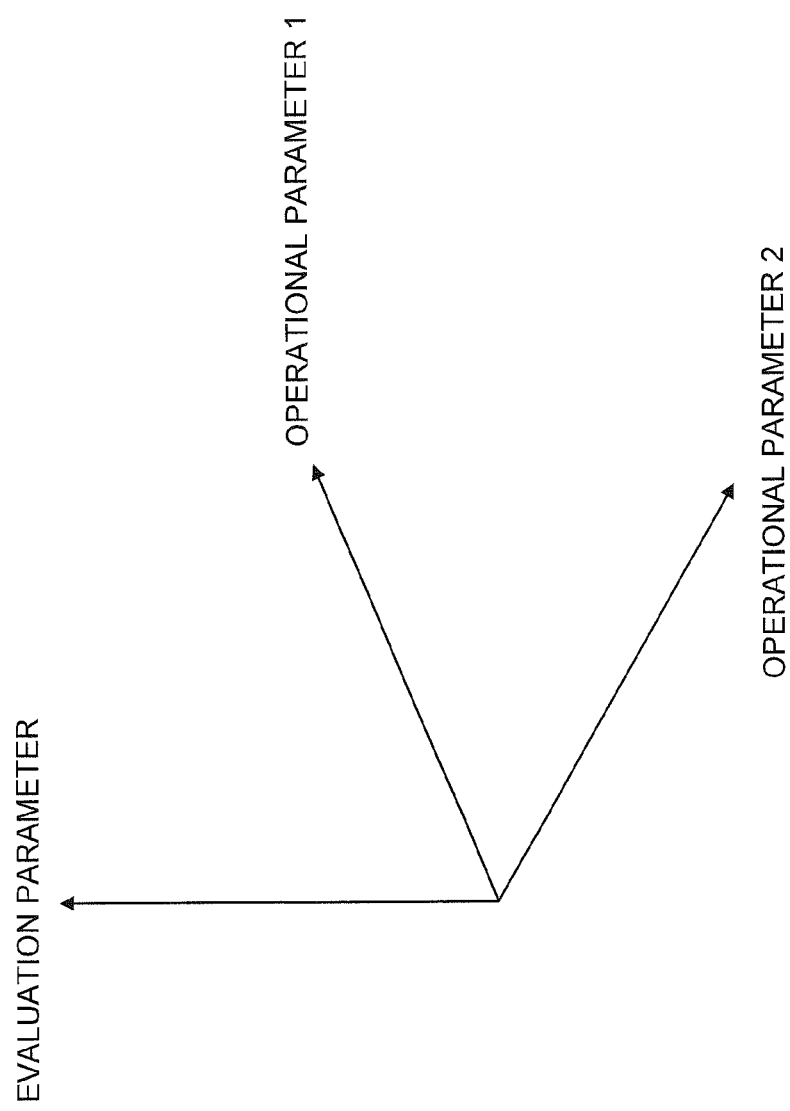
FIG. 8 is a diagram illustrating an evaluation graph according to a variation.

For example, in the above-described embodiment, the evaluation graph is a two-dimensional graph; however, besides, as illustrated in FIG. 8, the evaluation graph may be configured such that, for example, values of different types of operational parameters are taken on the two axes of X and Y, and a value of an evaluation parameter is taken on the other one axis (Z-axis). In this case, it is thought that configuring a display angle of the three-dimensional graph to be variable makes it easy for the operator to make evaluations. As the settings of the three axes of the three-dimensional graph, values of different evaluation parameters may be taken on two axes, and a value of an evaluation parameter may be taken on the other one axis.

Also, the above-described embodiment is configured to be able to change the types of the operational parameters and/or the evaluation parameters on one evaluation graph; however, an embodiment may be configured such that any operational parameter and/or evaluation parameter is not changed on one evaluation graph, but for each of the operational parameters and/or each of the evaluation parameters, an evaluation graph is displayed.

Further, the graph summary display screen may be adapted to display two or more different measurement result graphs, and the number of evaluation graphs is not limited to two, but may be one, or three or more.

In addition, the above-described embodiment is configured such that pieces of measurement result data are used to change values of the operational parameters within the predetermined ranges; however, an embodiment may be configured such that by changing values of the operational parameters to one or more typically values, values of the evaluation parameters are calculated.

Further, the particle size distribution measuring device is only required to be provided with functions as the interface device and the device main body in total, in which the interface device and the device main body may be physically integrated, and even if they are separated into two or more devices, the same working effect as in the above-described embodiment can be produced.

In addition, it should be appreciated that the present invention is not limited to any of the above-described embodiments, but can be variously modified without departing from the scope thereof.

REFERENCE SIGNS LIST

100: Particle size distribution measuring device
2: Device main body
3: Interface device
G1: Measurement result graph
G2, G3: Evaluation graph

The invention claimed is:

1. A particle size distribution measuring device comprising:
   an instrument main body that is structured to measure a particle size distribution of a sample; and
   an interface device that is structured to receive an input from an operator to perform drive control of the instrument main body, and to receive a measurement result from the instrument main body to display the measurement result, wherein
   the interface device is structured to display an evaluation graph and a measurement result graph on the same screen at a same time, the evaluation graph showing a relationship between values of operational parameters to be set to measure the particle size distribution and values of evaluation parameters which are obtained by using the measurement result from the instrument main body and correspond to respective values of the operational parameters, and the measurement result graph showing the measurement result from the instrument main body; and
   the interface device is further structured to display in the measurement result graph, a plurality of the measurement results corresponding to respective values of the operational parameters shown in the evaluation graph.

2. The particle size distribution measuring device according to claim 1, wherein
   the interface device is configured to be able to change types of the operational parameters and/or types of the evaluation parameters to be displayed in the graph.

3. The particle size distribution measuring instrument according to claim 1, wherein
   the operational parameters are a sample circulation rate, an operating time of an ultrasonic oscillator, an application time of an ultrasonic wave, an intensity of the ultrasonic wave, the number of data extraction times, the presence or absence of operation of the ultrasonic oscillator during the measurement, a sample concentration, or a refractive index of the sample; and
   the evaluation parameters are particle sizes, a standard deviation of the particle size distribution, a residual sum of squares of the particle size distribution, or a distribution function.

4. A method of measuring particle size distribution of a sample, the method comprising:
   providing an instrument main body structured to measure a particle size distribution of the sample;
   providing an interface device structured to receive an input to perform drive control of the instrument main body, receive a measurement result from the instrument main body, and display the measurement result;
   displaying, on the interface device, an evaluation graph and a measurement result graph on the same screen at a same time;
   wherein the evaluation graph shows a relationship between values of operational parameters to be set to measure the particle size distribution and values of evaluation parameters which are obtained by using the measurement result from the instrument main body and correspond to respective values of the operational parameters;
   wherein the measurement result graph shows the measurement result from the instrument main body; and
   wherein the displaying the evaluation graph and the measurement result graph comprises displaying, in the measurement result graph, a plurality of measurement results corresponding to respective values of the operational parameters shown in the evaluation graph.

* * * * *